(12) United States Patent
Kuhara

(10) Patent No.: US 8,818,487 B2
(45) Date of Patent: Aug. 26, 2014

(54) MAGNETIC RESONANCE IMAGING APPARATUS AND MAGNETIC RESONANCE IMAGING METHOD

(75) Inventor: Shigehide Kuhara, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 1290 days.

(21) Appl. No.: 12/579,500

(22) Filed: Oct. 15, 2009

(65) Prior Publication Data

US 2010/0094121 A1 Apr. 15, 2010

(30) Foreign Application Priority Data

Oct. 15, 2008 (JP) ................................. 2008-266560
Jun. 4, 2009 (JP) ................................. 2009-135179

(51) Int. Cl.
*A61B 5/05* (2006.01)

(52) U.S. Cl.
USPC ........... 600/410; 600/407; 600/421; 600/423; 600/424

(58) Field of Classification Search
USPC .......................... 600/407, 410, 421, 423, 424
See application file for complete search history.

(56) References Cited

U.S. PATENT DOCUMENTS

| | | | |
|---|---|---|---|
| 6,067,465 A * | 5/2000 | Foo et al. ....................... | 600/410 |
| 7,432,710 B2 | 10/2008 | Takei et al. | |
| 2007/0088212 A1 | 4/2007 | Takei et al. | |

FOREIGN PATENT DOCUMENTS

| | | |
|---|---|---|
| CN | 1432341 | 7/2003 |
| CN | 1943510 | 4/2007 |
| CN | 1943510 A | 4/2007 |
| CN | 1951323 | 4/2007 |
| JP | 2000-41970 | 2/2000 |
| JP | 2000-157507 | 6/2000 |
| JP | 2001-204712 | 7/2001 |
| JP | 2004-57226 | 2/2004 |
| JP | 2004-202043 | 7/2004 |
| JP | 2007-29250 | 2/2007 |
| JP | 2007-185250 | 7/2007 |
| JP | 2008-148806 | 7/2008 |

OTHER PUBLICATIONS

Carlson, et al., "Intermittent Mode CT Fluoroscopy-guided Biopsy of the Lung or Upper Abdomen with Breath-hold Monitoring and Feedback: System Development and Feasibility," *Radiology*, vol. 229, pp. 906-912 (2003).
Chinese Office Action mailed Feb. 5, 2010, in CN 2008-10095660.7, including English translation.
Chinese Office Action mailed Dec. 11, 2011, in CN 2010-10260781.X, including English translation.
First Office Action mailed on May 7, 2013 in JP 2008-266560 with English translation.
Office Action mailed Apr. 18, 2011 in Chinese Application No. CN 200910206344.7 with English translation.
U.S. Appl. No. 12/032,251, Shigehide Kuhara et al., filed Feb. 15, 2008.
U.S. Appl. No. 12/149,587, Shigehide Kuhara, filed May 5, 2008.

* cited by examiner

*Primary Examiner* — Unsu Jung
*Assistant Examiner* — Joel Lamprecht
(74) *Attorney, Agent, or Firm* — Nixon & Vanderhye PC

(57) ABSTRACT

A magnetic resonance imaging apparatus controls image reconstruction based on magnetic resonance signals collected when a peak of detected respiration level falls within an allowable range which changes based on a change in a plurality of peak values of a plurality detected respiration levels.

18 Claims, 12 Drawing Sheets

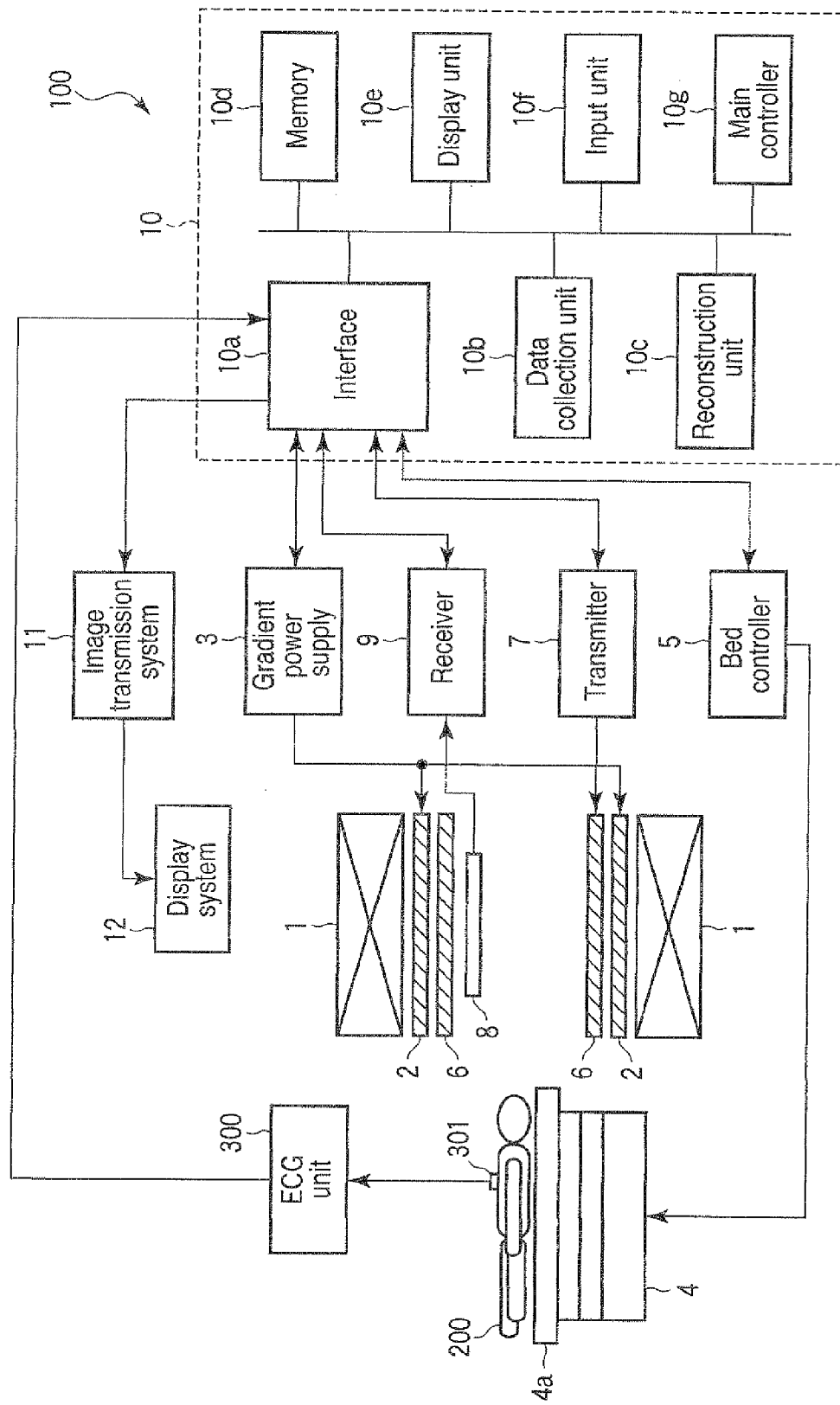
F I G. 4

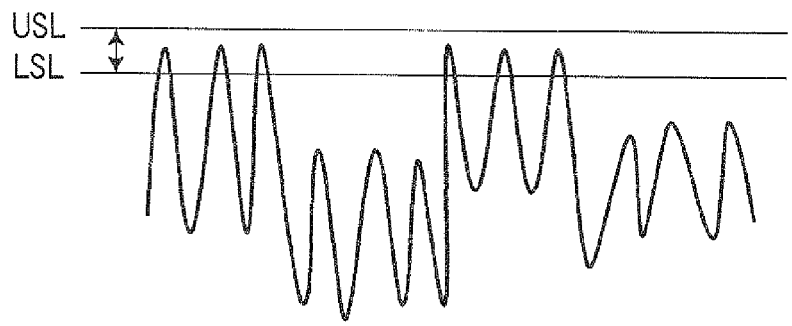
F I G. 20
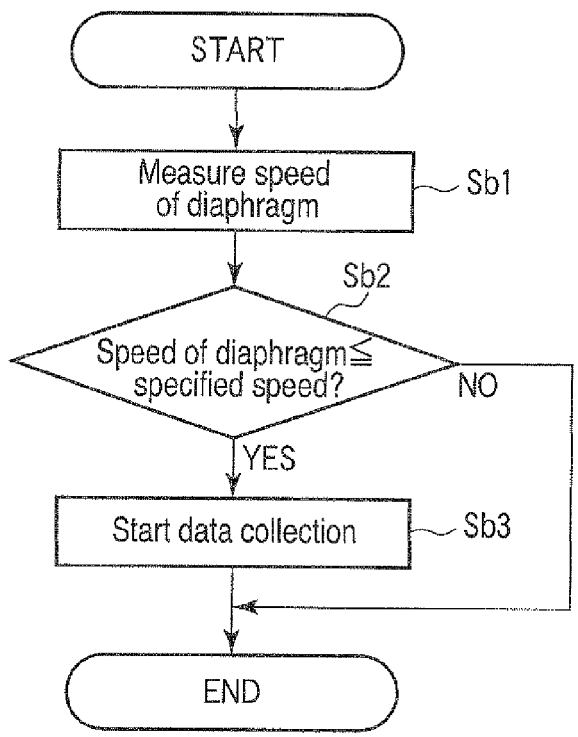
F I G. 21
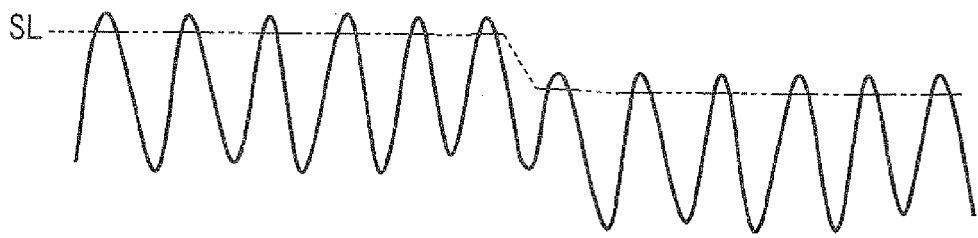
F I G. 22

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from prior Japanese Patent Applications No. 2008-266560, filed Oct. 15, 2008; and No. 2009-135179, filed Jun. 4, 2009, the entire contents of both of which are incorporated herein by reference.

BACKGROUND OF THE INVENTION

1. Field of the Invention

The present invention relates to a magnetic resonance imaging apparatus and a magnetic resonance imaging method that obtain an image in a subject based on a magnetic resonance signal produced in the subject.

2. Description of the Related Art

To image a coronary artery based on a magnetic resonance imaging (MRI) method, there is adopted a method which uses a three-dimensional (3D) steady-state free precession (SSFP) sequence to perform imaging in a breath-hold or natural aspiration state. In case of whole-heart MR coronary angiography (WH-MRCA) for imaging a coronary artery of an entire heart in particular, a change in position of the heart involved by breathing may affect image quality.

The rate of change in position of the heart involved by breathing is reduced when the respiration level is close to the peak thereof. Thus, a method of controlling data collection in accordance with the respiration level is used. That is, for example, the position of the diaphragm on the body axis can be detected from a signal which can be obtained by subjecting an NMR signal collected in such a region R as depicted in FIG. 1 to one-dimensional Fourier transformation. Since the position of the diaphragm on the body axis periodically fluctuates in accordance with breathing, plotting the periodically detected position of the diaphragm in time series enables obtaining such a monitor signal as depicted in FIG. 2 synchronized with a respiratory movement. Data is not collected while the peak of this monitor signal is out of an allowable range between an upper threshold USL and a lower threshold LSL as shown in FIG. 2, or data collected during such a period is not used for reconfiguring an image. Further, data collected during a period that the peak of the monitor signal is in the allowable range is utilized to reconstruct an image.

In a conventional example, the allowable range is set in accordance with a breathing state of a subject before or immediately after the start of an imaging operation, and it is not changed until the imaging operation is terminated.

The above-described technology is known from, e.g., JP-A 2000-041970 (KOKAI), JP-A 2000-157507 (KOKAI), or JP-A 2004-057226 (KOKAI).

However, when a respiration level is not fixed and is gradually reduced or gradually increased and the peak of the respiration level deviates from the allowable range as shown in, e.g., FIG. 3, an efficiency for collecting data which is effective for image reconstruction is lowered, an imaging time is prolonged, or an examination cannot be terminated in the worst case.

When the allowable range is sufficiently increased, a period that a high data collection efficiency can be maintained can be extended, but an increase in influence of deformation of the heart involved by the movement of the heart may possibly degrade image quality.

BRIEF SUMMARY OF THE INVENTION

In view of the above-described problem, enabling continuation of adequate imaging irrespective of a fluctuation in a breathing state of a subject has been demanded.

According to a first aspect of the present invention, there is provided a magnetic resonance imaging apparatus comprising: a collection unit which collects a magnetic resonance signal from the subject by applying a uniform static magnetic field to a subject and also applies a radio-frequency magnetic field and a gradient magnetic field to the subject in accordance with a predetermined pulse sequence; a reconstruction unit which reconstructs an image concerning the subject based on the magnetic resonance signal collected by the collection unit; a detection unit which detects a respiration level of the subject; a control unit which controls the reconstruction unit to reconstruct the image based on the magnetic resonance signal collected by the collection unit in a state wherein a peak of the detected respiration level falls within an allowable range; and a change unit which changes the allowable range based on a change in a plurality of peak values of a plurality of detected respiration levels.

According to a second aspect of the present invention, there is provided a magnetic resonance imaging apparatus comprising: a collection unit which collects a magnetic resonance signal from the subject by applying a uniform static magnetic field to a subject and also applies a radio-frequency magnetic field and a gradient magnetic field to the subject in accordance with a predetermined pulse sequence; a reconstruction unit which reconstructs an image concerning the subject based on the magnetic resonance signal collected by the collection unit; a detection unit which detects a respiration level of the subject; and a unit which controls the collection unit and the reconstruction unit to collect the magnetic resonance signal in accordance with a state wherein the rate of change of the detected respiration level is less than or equal to a predetermined rate, and to reconstruct the image based on the thus collected magnetic resonance signal.

According to a third aspect of the present invention, there is provided a magnetic resonance imaging apparatus comprising: a collection unit which collects a magnetic resonance signal from the subject by applying a uniform static magnetic field to a subject and also applies a radio-frequency magnetic field and a gradient magnetic field to the subject in accordance with a predetermined pulse sequence; a reconstruction unit which reconstructs an image concerning the subject based on the magnetic resonance signal collected by the collection unit; a detection unit which repeatedly detects a respiration level of the subject; a reconstruction control unit which controls the reconstruction unit to reconstruct the image based on the magnetic resonance signal collected by the collection unit in a state wherein a peak of the respiration level detected by the respiration level detection unit falls within an allowable range; a peak detection unit which repeatedly detects peak values of the respiration level detected by the respiration level detection unit in 1 cycle of a respiratory motion of the subject; an allowable range setting unit which sets the allowable range based on an average value of the peak values during a first period that the plurality of respiration levels are detected by the respiration level detection unit; and a setting control unit which controls the allowable range setting unit in such a manner that the allowable range setting unit sets a setting frequency for setting the allowable range in accordance with a frequency of the respiratory motion of the subject and sets the allowable range with the setting frequency.

According to a fourth aspect of the present invention, there is provided a magnetic resonance imaging apparatus, comprising: a collection unit which collects a magnetic resonance signal from the subject by applying a uniform static magnetic field to a subject and also applies a radio-frequency magnetic field and a gradient magnetic field to the subject in accordance with a predetermined pulse sequence; a reconstruction unit which reconstructs an image concerning the subject based on the magnetic resonance signal collected by the collection unit; a detection unit which repeatedly detects a respiration level of the subject; a control unit which controls the reconstruction unit to reconstruct the image based on the magnetic resonance signal collected by the collection unit in a state wherein a peak of the respiration level detected by the respiration level detection unit falls within an allowable range; a trackable range setting unit which sets a trackable range based on the respiration level detected by the respiration level detection unit when or before the collection unit starts collecting the magnetic resonance signal which is used for the reconstruction by the reconstruction unit; and an allowable range setting unit which sets the allowable range within the trackable range based on an average value of the peak values during a period that the respiration level detection unit detects the plurality of respiration levels.

According to a fifth aspect of the present invention, there is provided a magnetic resonance imaging method comprising: collecting a magnetic resonance signal from the subject by applying a uniform static magnetic field to a subject and also applying a radio-frequency magnetic field and a gradient magnetic field to the subject in accordance with a predetermined pulse sequence; repeatedly detecting a respiration level of the subject; performing control to reconstruct the image based on the magnetic resonance signal collected by the collection unit in a state wherein a peak of the detected respiration level falls within an allowable range; and changing the allowable range based on a change in a plurality of peak values of a plurality of detected respiration levels.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a view showing a configuration of a magnetic resonance imaging apparatus (an MRI apparatus) according to first to forth embodiments of the present invention;

FIG. 20 is a view showing a setting example of the allowable range when the respiratory variation is large in the third embodiment;

FIG. 21 is a view showing a processing procedure of the main controller depicted in FIG. 4 according to a fourth embodiment;

FIG. 22 is a view for explaining an effect of the fourth embodiment;

DETAILED DESCRIPTION OF THE INVENTION

Figure 1:
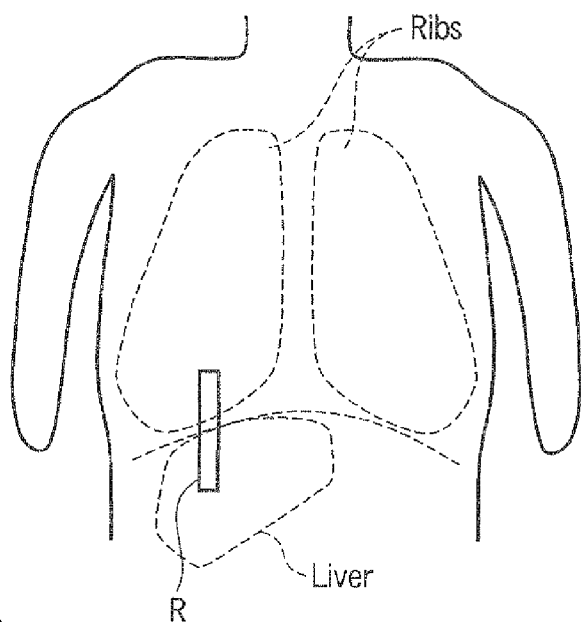
FIG. 1 is a view showing a region where an NMR signal used for detecting a respiration level is collected.
Figure 2:
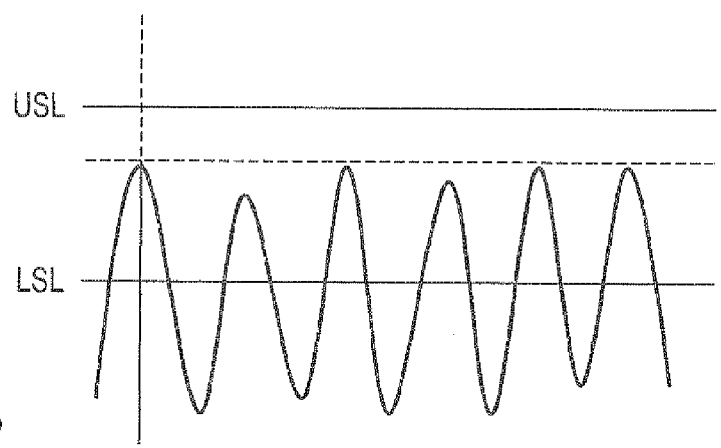
FIG. 2 is a view showing an example of a monitor signal.
Figure 3:
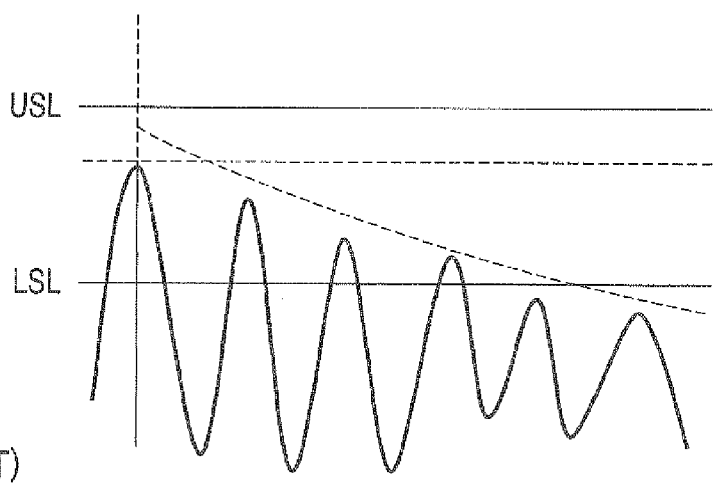
FIG. 3 is a view showing an example of a state wherein the peak of the monitor signal deviates from an allowable range.

First to fourth embodiments according to the present invention will now be described hereinafter with reference to the accompanying drawings.

FIG. 4 is a view showing a configuration of a magnetic resonance imaging apparatus (an MRI apparatus) according to the first to fourth embodiments. The MRI apparatus 100 includes a static field magnet 1, a gradient coil unit 2, a gradient power supply 3, a bed 4, a bed controller 5, a transmission RE coil 6, a transmitter 7, a reception RE coil 8, a receiver 9, a computer system 10, a image transmission system 11, and a display system 12.

The static field magnet 1 has a hollow cylindrical shape, and generates a uniform static magnetic field in an inner space thereof. As this static field magnet 1, a permanent magnet or a superconducting magnet is used, for example.

The gradient coil unit 2 has a hollow cylindrical shape and is arranged inside the static field magnet 1. In the gradient coil unit 2, three types of coils associated with respective axes X, Y, Z orthogonal to each other are combined. In the gradient coil unit 2, the three types of coils individually receive supply of a current from the gradient power supply 3 and generate gradient magnetic fields whose magnetic field intensities differ along the respective axes X, Y, and Z. It is to be noted that a direction of the axis Z is the same direction as a static magnetic field, for example. The gradient magnetic fields in the respective axes X, Y, and Z are arbitrarily used as, e.g., a slice selection gradient magnetic field Gs, a phase encoding gradient magnetic field Ge, and a readout gradient magnetic field Gr, respectively. The slice selection gradient magnetic field Gs is utilized for arbitrarily determining an imaging cross section. The phase encoding gradient magnetic field Ge is utilized for changing a phase of an NMR signal in accordance with the spatial position. The readout gradient magnetic field Gr is utilized for changing a frequency of the NMR signal in accordance with the spatial position.

A subject 200 lies down on a top panel 4a of the bed 4 to be fed into the hollow of the gradient coil unit 2. The top panel 4a included in the bed 4 is driven by the bed controller 5 to move along a longitudinal direction and a vertical direction thereof. Usually, the bed 4 is installed in such a manner that this longitudinal direction becomes parallel to a central axis of the static field magnet 1.

The transmission RF coil 6 is arranged inside the gradient coil unit 2. The transmission RF coil 6 receives supply of a radio-frequency pulse from the transmitter 7 to generate a radio-frequency magnetic field.

The transmitter 7 transmits a radio-frequency pulse corresponding to a Larmor frequency to the transmission RF coil 6.

The reception RF coil 8 is arranged inside the gradient coil unit 2. The reception RF coil 8 receives the NMR signal emitted from the subject due to an influence of the radio-frequency magnetic field. An output signal from the reception RF coil 8 is input to the receiver 9.

The receiver 9 generates NMR signal data based on the output signal from the reception RF coil 8.

The computer system 10 has an interface 10a, a data collection unit 10b, a reconstruction unit 10c, a memory 10d, a display unit 10e, an input unit 10f, and a main controller 10g.

To the interface 10a are connected the gradient power supply 3, the bed controller 5, the transmitter 7, the reception RF coil 8, the receiver 9, the image transmission system 11, the ECG unit 300, and others. The interface 10a has each interface circuit associated with each of these connected units, and inputs/outputs signals transmitted or received between the respective units and the computer system 10. It is to be noted that the ECG unit 300 inputs an ECG signal of the subject 200 through an ECG sensor disposed to the subject 200, and outputs an R-wave detection signal at a timing that an R-wave is produced in the ECG signal. The interface 10a receives this R-wave detection signal and informs the main controller 10g of this signal.

The data collection unit 10b collects a digital signal output from the receiver 9 through the interface 10a. The data collection unit 10b stores the collected digital signal, i.e., NMR signal data in the memory 10d.

Therefore, in this MRI apparatus 100, the static field magnet 1, the gradient coil unit 2, the gradient power supply 3, the transmission RE coil 6, the transmitter 7, the reception RE coil 8, the receiver 9, and the data collection unit 10b function as a collection unit that collects magnetic resonance signals from the subject 200.

The reconstruction unit 10c executes post-processing, i.e., reconstruction such as Fourier transformation with respect to the NMR signal data stored in the memory 10d to obtain spectrum data or image data of a desired nuclear spin in the subject 200.

The memory 10d stores the NMR signal data and the spectrum data or the image data in accordance with each patient.

The display unit 10e displays various kinds of information, e.g., the spectrum data or the image data under control of the main controller 10g. As the display unit 10e, a display device such as a liquid crystal display instrument can be utilized.

The input unit 10f accepts various kinds of commands or information inputs from an operator. As the input unit 10f, a pointing device such as a mouse or a trackball, a selection device such as a mode changeover switch, or an input device such as a keyboard can be appropriately utilized. Further, the input unit 10f accepts a specification of an excited slice or an excited slab as an imaging region of, e.g., an entire heart or a synchronization target region such as the diaphragm from the operator.

The main controller 10g has a non-illustrated CPU or a memory and controls the MRI apparatus 100. Furthermore, the main controller 10g generates an image signal of an image which represents whether a respiration level falls within the allowable range. This image signal is, e.g., a National Television System Committee (NTSC) signal.

The image transmission system 11 transmits the image signal generated by the main controller 10g by using light.

The display system 12 displays an image based on the image signal in such a manner that the subject 200 in an imaging state can be visually confirmed.

(First Embodiment)

In a first embodiment, the main controller 10g has a plurality of functions mentioned below. It is to be noted that the plurality of functions can be realized by allowing a processor included in the main controller 10g to execute a program.

One of the functions is to control each relevant portion so that an NMR signal that is used for detecting a respiration level of the subject 200 (which will be referred to as a monitoring NMR signal hereinafter) can be acquired by the data collection unit 10b. One of the functions is to detect a respiration level of the subject 200 based on the monitoring NMR signal acquired by the data collection unit 106. One of the functions is to control each relevant portion so that an NMR signal that is used for reconstructing an image (which will be referred to as a reconstruction NMR signal hereinafter) can be collected by the data collection unit 10b when the detected respiration level falls within the allowable range. One of the functions is to detect the position of the diaphragm of the subject 200 based on the monitoring NMR signal. One of the functions is to measure the offset of the detected position of the diaphragm from a reference position. One of the functions is to control each relevant portion so that a range where the reconstruction NMR signal is collected is moved for a distance associated with the measured offset. One of the functions is to change a central level of the allowable range based on the detected change in respiration level.

An operation of the MRI apparatus 100 according to the first embodiment will now be described.

In this first embodiment, the MRI apparatus 100 executes the WH-MRCA utilizing the RMC method in accordance with a known sequence.

Figure 5:
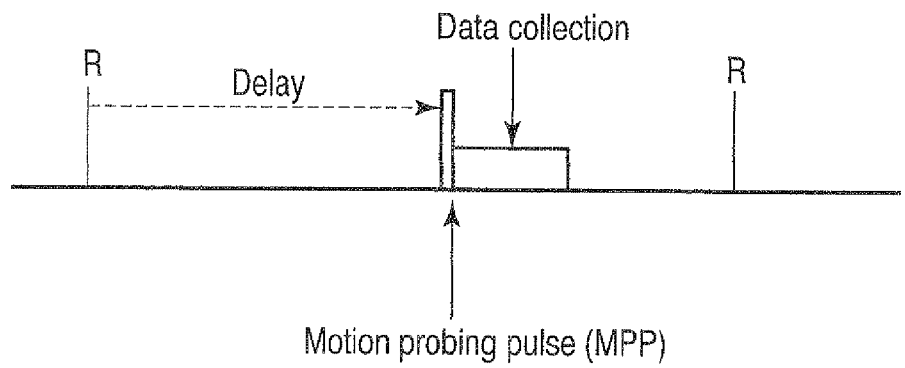
FIG. 5 is a view showing an example of a sequence of WH-MBCA utilizing an RMC method.

FIG. 5 is a view showing an example of the sequence of the WH-MRCA utilizing the RMC method.

The RMC method is usually performed with electrocardiographic synchronization. That is, the sequence is carried out in synchronization with an R-wave detection signal output from the ECG unit 300. Specifically, after elapse of a fixed delay time from the appearance of an R-wave in an electrocardiographic signal from the generation the R-wave detection signal), a motion probing pulse (MPP) as the monitoring NMR signal is collected. Furthermore, immediately after this collection, a period during which data used for imaging is collected is set. However, the electrocardiographic synchronization is not required, and the MPP may be collected in a fixed repetition cycle.

The MPP can be acquired in regard to such a region R as depicted in FIG. 1 without applying, e.g., a phase encoding gradient magnetic field. Thus, the position of the diaphragm on the body axis can be detected from a signal obtained by performing one-dimensional Fourier transformation to this MPP. Since the position of the diaphragm on the body axis periodically fluctuates in accordance with breathing, the thus detected position of the diaphragm can be utilize as the respiration level as it is.

Thus, the main controller 10g detects the position of the diaphragm, i.e., the respiration level based on the MPP. Moreover, the main controller 10g controls each relevant portion in such a manner that data can be collected during a subsequent data collection period only when the peak of the detected respiration level falls within a predetermined allowable range. Alternatively, the main controller 10g controls each relevant portion in such a manner that data can be collected in the subsequent data collection period irrespective of whether the peak of the detected respiration level falls within the allowable range, but it validates the collected data only when the peak of the detected respiration level falls within the allowable range. Additionally, when collecting data, the main controller 10g measures the offset of the detected position of the diaphragm from a predetermined reference position, and controls each relevant portion to adjust a range where the reconstruction NMR signal is collected (an imaging range) in such a manner that this offset can be compensated. However, this adjustment of the imaging range can be omitted.

It is to be noted that the allowable range is initialized based on the respiration level of the subject 200 before starting the imaging. This initialization may be performed by the main controller 10g in response to an instruction by an operator, or it may be automatically carried out by the main controller 10g. Although the initial allowable range may be arbitrary, it is typically determined to have a fixed width with a value close to the average value of peaks of respiration levels being determined as a central level. Further, the reference position is also initialized as the position of the diaphragm before starting the imaging. The initialization of the reference position may be carried out by the main controller 10g in response to an instruction from the operator, or it may be automatically performed by the main controller 10g. Furthermore, the imaging range is also initialized before starting the imaging. The initialization of the imaging range may be performed by the main controller 10g in response to an instruction from the operator, or it may be automatically carried out by the main controller 10g. It is to be noted that the timing before starting imaging in this description means a timing before starting an operation for actually collecting the reconstruction NMR signal. To detect the position of the diaphragm before starting the imaging, it is good enough to repeat the sequence depicted in FIG. 5 for a few times prior to starting the sequence shown in FIG. 5 for collecting the reconstruction NMR signal. In this case, the data collected during the data collection period is discarded, and the MPP alone is used for detecting the position of the diaphragm. Alternatively, the collection of the MPP alone may be repeated for a few times without effecting the data collection depicted in FIG. 5.

Figure 6:
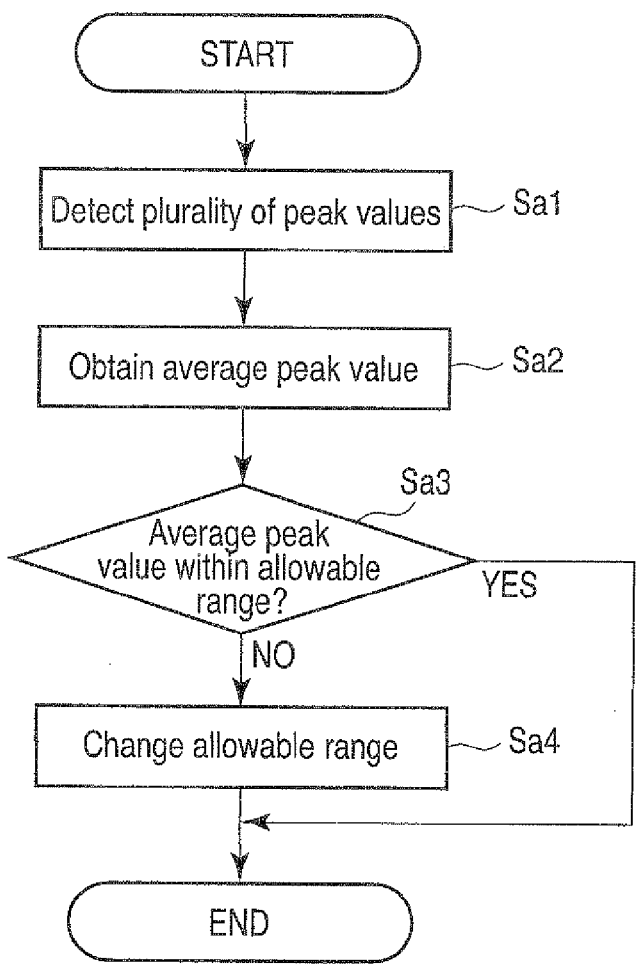
FIG. 6 is a view showing a processing procedure of a main controller depicted in FIG. 4 according to the first embodiment.

The main controller 10g carries out such processing as shown in FIG. 6 in accordance with a predetermined timing in parallel to the above-described imaging. A timing for effecting this processing may be arbitrary, but executing the processing every time the new respiration level is detected or every time a fixed time elapses can be considered, for example.

Figure 7:
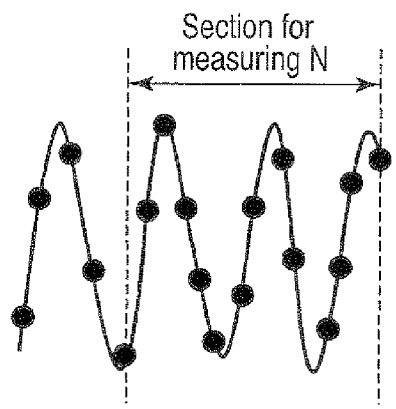
FIG. 7 is a view showing an example of a change in respiration level to which is reference is made to obtain an average peak value.

At step Sa1, the main controller 10g detects a plurality of peak values of respiration levels based on previously detected respiration levels at such points N as depicted in FIG. 7, for example. N may be an arbitrary integer, but a plurality of respiration cycles must be included in a time required to measure respiration levels at the points N in order to enable detecting the plurality of peak values.

The peak value of the respiration level can be detected from actually detected respiration levels as a respiration level higher than both previous and subsequent respiration levels. That is, each of the respiration levels at the points N is compared with each of previous and subsequent respiration levels thereof, and the respiration level higher than both the previous and subsequent respiration levels is determined as the peak value. It is to be noted that, if the number of points for the respiration levels detected in 1 respiratory cycle is sufficiently large, an accuracy for the peak value detection may be improved by comparing each respiration level with a plurality of previous and subsequent respiration levels.

Figure 8:
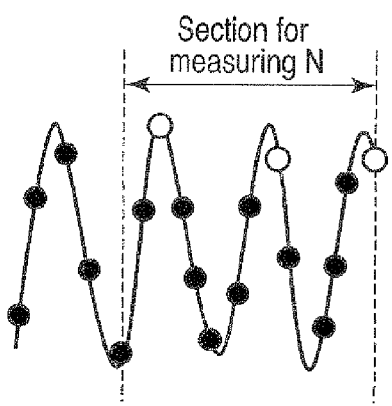
FIG. 8 is a view showing a state wherein peak values are detected from actually detected respiration levels as depicted in FIG. 7.

FIG. 8 is a view showing a state wherein peak values are detected from actually detected respiration levels as shown in FIG. 7. In FIG. 8, each detected peak value is represented by a open circle.

However, when such a sequence as shown in FIG. 5 is detected, the respiration level detection is performed once per heartbeat. That is, the respiration level detection is carried out for several times only per breath. There is no guarantee that the peak value of the respiration level is actually detected. Therefore, according to the above-described method, processing is easy, but an error in a detected peak value may possibly become large.

Thus, to reduce the error in the peak value, the peak value may be detected by the interpolation using, e.g., polynomial approximation or a spline function.

Figure 9:
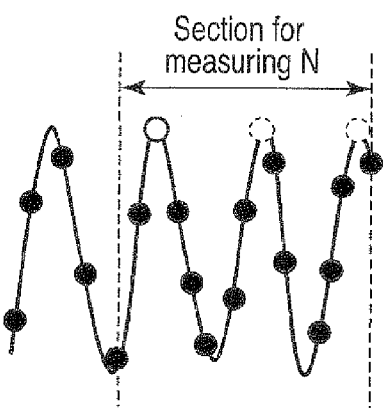
FIG. 9 is a view showing a state wherein a peak value is detected by interpolation based on the actually detected respiration levels as shown in FIG. 7.

FIG. 9 is a view showing a state wherein peak values are detected by the interpolation based on actually detected respiration levels as shown in FIG. 7. In FIG. 9, the detected peak values are represented by open circles. In these peak values, each value detected by the interpolation is indicated by a broken line.

Figure 10:
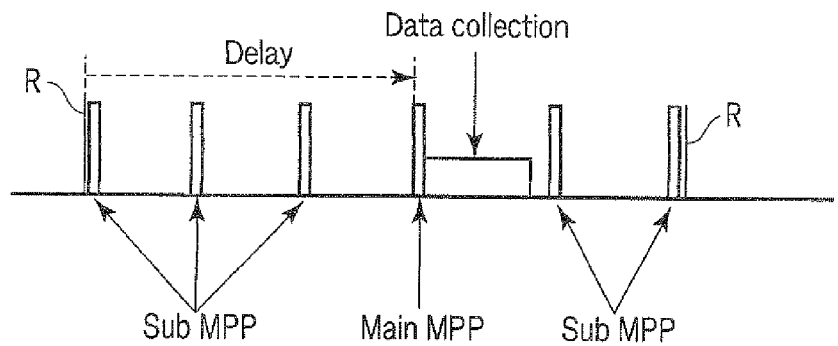
FIG. 10 is a view showing a modification of a sequence when WH-MRCA is performed.

It is to be noted that a respiration level detection frequency may be increased by adopting such a sequence as shown in FIG. 10. When the respiration level detection frequency is increased in this manner, an error in the peak value can be reduced even though any one of the above-described methods is utilized to detect the peak value.

In the sequence depicted in FIG. 10, a plurality of MPPs are collected per heartbeat. The plurality of MPPs are classified into a main MPP which is collected immediately before a data collection period in an imaging region and a sub-MPP which is collected at a timing different from that of the main MPP while avoiding the data collection period. The sub-MPP may be collected either before or after the main MPP in a period excluding the data collection period in the imaging region. For example, a plurality of sub-MPPs may be collected before the main MPP. Further, a plurality of MPPs (including not only a sub-MPP but also a main MPP) may be collected at equal intervals per heat rate. In this case, when any one in the plurality of MPPs set at equal intervals is included in the data collection period for the imaging region, this MPP is prevented from being collected.

At step Sa2, the main controller 10g obtains the average value of the plurality of peak values detected at step Sa1 (which will be referred to as the average peak value hereinafter).

At step Sa3, the main controller 10g confirms whether the average peak value obtained at step Sa2 falls within the allowable range.

If the average peak value is in the allowable range, the main controller 10g terminates the processing in FIG. 6 as it is. Therefore, in this case, the allowable range is not changed.

If the average peak value deviates from the allowable range, the main controller 10g advances from step Sa3 to step Sa4. At step Sa4, the main controller 10g changes the allowable range based on the average peak value.

Figure 11:
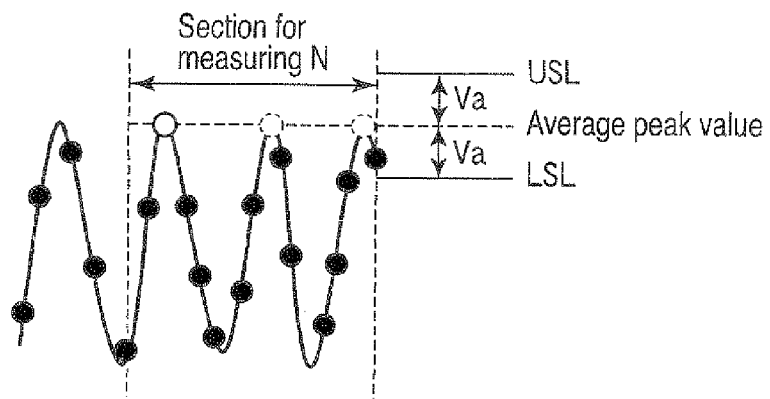
FIG. 11 is a view showing an example of a state wherein a new allowable range is determined.

FIG. 11 is a view showing an example of a state wherein the new allowable range is determined.

In this example depicted in FIG. 11, a value obtained by adding a specified value Va to the average peak value is determined as an upper threshold USL, and a value obtained by subtracting the specified value Va from the average peak value is determined as a lower threshold LSL. The specified value Va is ½ of a width of the allowable range set on the initial stage. Therefore, in this example depicted in FIG. 11, the allowable range is shifted in such a manner that the central level alone is adapted to a newly obtained average peak value without changing the width of the allowable range.

Figure 12:
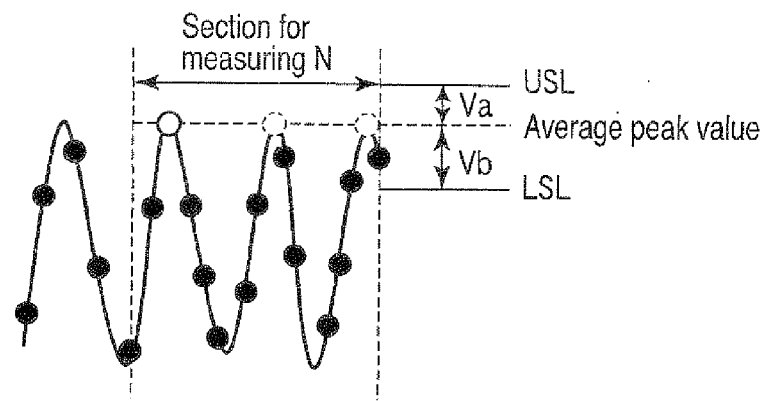
FIG. 12 is a view showing another example of the state wherein the new allowable range is determined.

FIG. 12 is a view showing another example of the state wherein the new allowable range is determined.

In this example depicted in FIG. 12, a value obtained by adding the specified value Va to the average peak value is determined as the upper threshold USL, and a value obtained by subtracting a specified value Vb from the average peak value is determined as the lower threshold LSL. The specified value Va or Vb is a value obtained by multiplying the allowable range set on the initial stage by a coefficient Ca or Cb. The coefficients Ca and Cb are preset in such a manner that Ca<Cb is achieved. Therefore, in this example depicted in FIG. 12, the allowable range is shifted in such a manner that the central level alone is adapted to a newly obtained average peak value without changing the width of the allowable range, which is the same as the example depicted in FIG. 11. However, in the example depicted in FIG. 12, the allowable range is set in such a manner that a margin from the average peak value to the lower threshold LSL becomes larger than a margin from the average peak value to the upper threshold USL. Each of the coefficients Ca and Cb may be a fixed value or a value arbitrarily specified by a user.

When this method depicted in FIG. 12 is adopted, a probability that a respiration level which is detected later falls within the allowable range can be increased as compared with the case where the method depicted in FIG. 11 is adopted, thus improving a detection efficiency.

Figure 13:
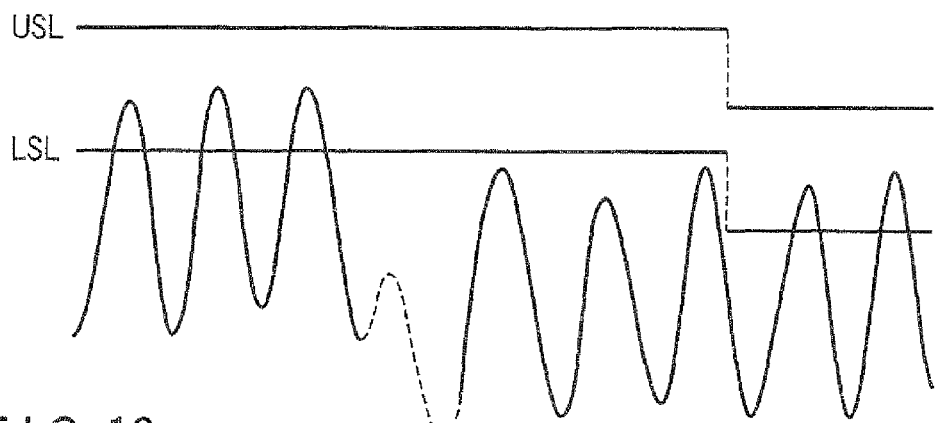
FIG. 13 is a view showing an example of a state wherein the allowable range is changed.

Therefore, the allowable range is changed as shown in, e.g., FIG. 13 in accordance with a change in respiration level.

When the allowable range is changed in this manner, the peak of the respiration level which has once deviated from the allowable range can again fall within the allowable range as shown in FIG. 13. Therefore, the imaging can be continued.

It is to be noted that this first embodiment can be applied to all natural aspiration imaging, breath-hold imaging, and multi-breath-hold imaging.

In breath-hold imaging and multi-breath-hold imaging, breath must be held in such a manner that the respiration level of the subject falls within the allowable range in the conventional technology. Further, when the breath is held in a state wherein the respiration level is out of the allowable range, effective data cannot be collected in this breath-hold period. However, using both the first embodiment and multi-breath-hold imaging enables changing the allowable range in accordance with the respiration level at which the breath is held, and hence data can be collected only if the breath is held. As a result, imaging time can be reduced. Furthermore, the subject can hold his/her breath without worrying about the allowable range. Moreover, as a result of the reduction in imaging time and the improvement in flexibility of breath-holding, burden on the subject can be greatly decreased.

In this case, however, a time lag until the allowable range is changed after the start of breath-holding increases as a value of N rises. That is, a percentage of a fruitless time that data cannot be collected during a breath-hold time increases. Therefore, it is preferable to set the value N when performing breath-hold imaging or multi-breath-hold imaging to be smaller than that when performing imaging with natural aspiration.

Since adopting breath-hold imaging or multi-breath-hold imaging enables collecting data while rarely producing a change in the position of the heart, which is affected by respiration, a highly accurate image can be reconstructed from the thus collected data.

Additionally, in case of multi-breath-hold imaging, an operation for data collection may be performed during an intermittent breath-hold period only, and the operation for data collection may be avoided during a natural aspiration period, and the operation for data collection may be continued irrespective of respiration state. However, according to the latter case, since RF excitation is continuously carried out, contrast of a reconstructed image is stabled.

Further, data collected when the respiration level falls within the allowable range during the breath-hold period alone may be used as data effective for image reconstruction, or data collected when the respiration level falls within the allowable range irrespective of the breath-hold period may be used as data effective for image reconstruction. However, according to the latter case, data effective for image reconstruction can be collected even during the natural aspiration period between breath-hold periods, thereby reducing the imaging time.

Meanwhile, in breath-hold imaging or multi-breath-hold imaging, a sound generation apparatus may be used to instruct the subject to start breath-holding. In this case, the allowable range can be rapidly changed by executing processing for changing the allowable range in cooperation with an operation of the sound generation apparatus.

Several ingenuities in the first embodiment will now be described hereinafter.

Figure 14:
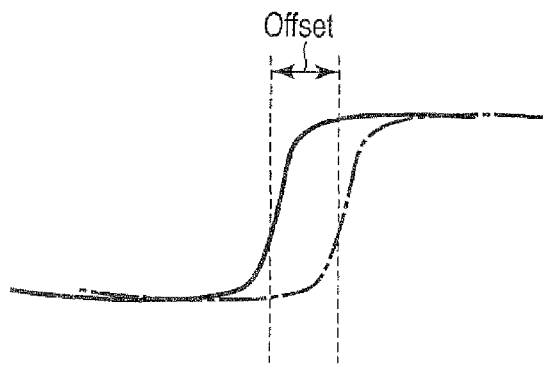
FIG. 14 is a view showing a state wherein an offset to which reference is made to adjust an imaging range is obtained.

(1) As explained above, adjustment of the imaging range is carried out by measuring the offset of the detected position of the diaphragm from the predetermined reference position to compensate for this offset. In regard to the measurement of the offset, a Fourier transformation signal obtained to detect the respiration level when a reference imaging range is set is held as a reference signal, and a Fourier transformation signal obtained to detect the respiration level every time data is collected is compared with the reference signal as shown in FIG. 14 to calculate the offset. It is to be noted that the reference signal is indicated by a solid line and the Fourier transformation signal when collecting data is indicated by an alternate long and short dash line in FIG. 14. Further, to measure the offset, specifically, a known method such as an edge detection method or a cross-correlation method is utilized.

Specifically, for example, as an initialized imaging range, it is good enough to set an imaging range which is adjusted as a range moved for a distance associated with the offset. In this case, even if the allowable range is changed, the reference position is not varied. That is, even if the allowable range is changed, the reference signal is not again acquired. However, the reference signal may be again acquired to update the reference position every time the allowable range is changed. In this case, however, the positional relationship between the reference position and the initialized imaging range varies before and after updating the reference position. Thus, when the reference position is updated, the correspondence between the offset and the distance is changed.

It is to be noted that the position of the heart changes in synchronization with the movement of the diaphragm, but a distance of the diaphragm does not necessarily coincide with a variation of the heart position. Therefore, the distance is obtained by multiplying the offset by a coefficient. That is, the distance in the initial state wherein the reference position is not changed is obtained by, e.g., multiplying the calculated offset by a predetermined coefficient. However, after the reference position is changed, a value obtained by adding the distance from the initial reference position of the latest reference position to the calculated offset is multiplied by the predetermined coefficient to acquire the distance.

It is to be noted that the coefficient in this example may be changed in accordance with the respiration level. Specifically, when the respiration level is high or low as compared with a case where the respiration level is approximately medium, the variation in position of the heart is reduced due to the influence of surrounding organs, and hence the coefficient is changed in accordance with the respiration level while considering such a relationship.

(2) Not only the position of the imaging target region of each of some parts, e.g., the heart is changed but also the shape is changed in accordance with the respiration level. For example, the heart becomes large as the position of the diaphragm is lowered. Therefore, data concerning imaging target regions having different shapes is collected before and after changing the allowable range. In regard to this data collection, any measure does not have to be taken when the rate of change in shape of each imaging target region is low or image quality is not important. However, when the rate of change in shape of the imaging target region is high or image quality is important, taking a measure is desirable.

As one of such measures, scale-up, scale-down, or affine transformation is performed with respect to each data at a ratio associated with the offset in the allowable range when each data is collected, and then an image is reconstructed based on such processed data. The scale-up, the scale-down, or the affine transformation can be executed by, e.g., the reconstruction unit 10c or the main controller 10g.

Figure 15:
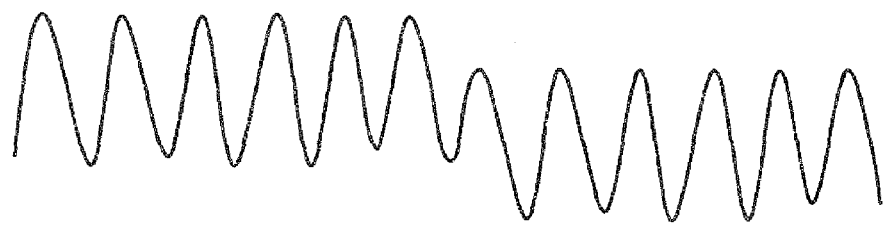
FIG. 15 is a view showing an example of a change in respiration level when a respiratory variation is small.
Figure 16:
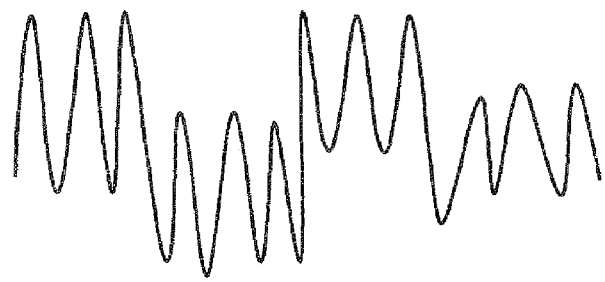
FIG. 16 is a view showing an example of a change in respiration level when the respiratory variation is large.

(3) To enable coping with, e.g., a situation that a respiratory variation quickens in midstream, the number N of the respiration levels to which reference is made to obtain the average peak value may be changed in accordance with a degree of the respiratory variation. That is, assuming that the number of the respiration levels to which reference is made to obtain the average peak value is represented as Na when a respiratory variation is small as shown in, e.g., FIG. 15 and the same is represented as Nb when a respiratory variation is large as shown in, e.g., FIG. 16, Na>Nb is set. To realize this relationship, the main controller 10g obtains an index value representing a degree of the respiratory variation. Further, based on comparison between this index value and a predetermined threshold, one of Na and Nb is adopted. Na, Nb, and the threshold may be arbitrarily determined by a designer or a user of the MRI apparatus 100. The respiratory variation specifically includes a change in depth of respiration, a change in average level of respiration, or a change in respiration rate. As an index value for a change in depth of respiration, a variance of the respiration level detected during a predetermined period can be used, for example. As an index value for a change in average level of respiration, the average value of respective respiration levels or the difference of variances of the same during predetermined two periods can be used, for example. As an index value for a change in respiration rate, the number of peaks detected within, e.g., a unit time can be used. Of course, a candidate for the number of respiration levels to which reference is made to obtain the average peak value can be set to M (M is an integer greater than or equal to 3), a threshold can be set to M−1, and the number of the respiration levels to which reference is made to obtain the average peak value can be changed on three or more stages. Alternatively, a value of N may be obtained based on an expression that determines the value of N in accordance with an index value.

(Second Embodiment)

In a second embodiment, a main controller 10g includes a plurality of functions mentioned below. It is to be noted that the plurality of functions can be realized by allowing a processor included in the main controller 10g to execute a program.

One of the functions is to control each relevant portion so that a monitoring NMR signal can be acquired by a data collection unit 10b. One of the functions is to detect a respiration level of a subject 200 based on the monitoring NMR signal acquired by the data collection unit 10b. One of the functions is to control each relevant portion in such a manner that a reconstruction NMR signal is collected by the data collection unit 10b when the detected respiration level falls within an allowable range. One of the functions is to detect the position of the diaphragm of a subject 200 based on the monitoring NMR signal. One of the functions is to measure the offset of the detected position of the diaphragm from a reference position. One of the functions is to control each relevant portion in such a manner that a range where the reconstruction NMR signal is collected is moved for a distance associated with the measured offset. One of the functions is to change a width of the allowable range based on the detected respiratory variation.

An operation of the MRI apparatus 100 according to the second embodiment will now be described.

The operation in the second embodiment is equal to that in the first embodiment in many aspects. Furthermore, the operation in the second embodiment is different from that in the first embodiment in a method of changing an allowable range.

The main controller 10g obtains an index representing a degree of a respiratory variation in place of performing such processing as depicted in FIG. 6 in parallel to execution of the imaging described in conjunction with the first embodiment. As this index, a variance of respiration levels detected during a predetermined period, the average value of respiration levels in two predetermined periods, or the difference of variances of the same can be used.

Figure 17:
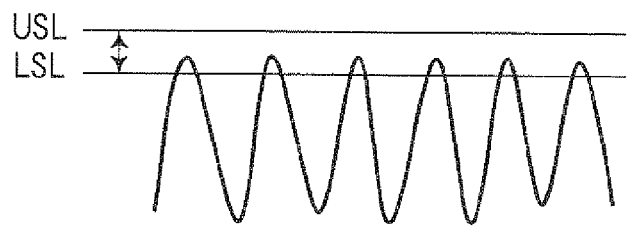
FIG. 17 is a view showing a setting example of an allowable range when a respiratory variation is small in a second embodiment.
Figure 18:
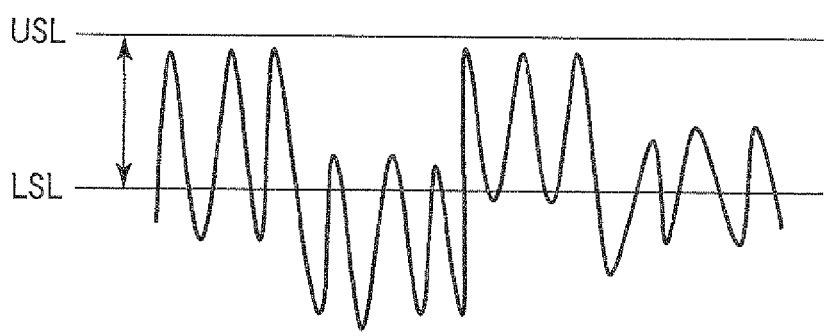
FIG. 18 is a view showing a setting example of the allowable range when the respiratory variation is large in the second embodiment.

Moreover, the main controller 10g changes a width of the allowable range in accordance with a magnitude of the obtained index. Specifically, as shown in FIGS. 17 and 18, a width of the allowable range when a respiratory variation is large is increased beyond that of the allowable range when the respiratory variation is small.

According to this second embodiment, data can be collected while increasing an adjustment accuracy for the imaging range when the respiratory variation is small, and the data collection can be continued when the respiratory variation is large.

This second embodiment is useful when examination efficiency is more important than image quality.

(Third Embodiment)

A main controller 10g according to a third embodiment has a plurality of functions mentioned below. It is to be noted that the plurality of functions can be realized by allowing a processor included in the main controller 10g to execute a program.

One of the functions is to control each relevant portion in such a manner that a monitoring NMR signal is acquired by a data collection unit 10b. One of the functions is to detect a respiration level of a subject 200 based on the monitoring NMR signal acquired by the data collection unit 10b. One of the functions is to control each relevant portion in such a manner a reconstruction NMR signal can be collected by the data collection unit 10b when the detected respiration level falls within an allowable range. One of the functions is to detect the position of the diaphragm of the subject 200 based on the monitoring NMR signal. One of the functions is to measure the offset of the detected position of the diaphragm from a reference position. One of the functions is to control each relevant portion in such a manner that a range where the reconstruction NMR signal is collected is moved for a distance associated with the measured offset. One of the functions is to change a width of the allowable range based on the detected respiratory variation.

An operation of the MRI apparatus 100 according to the third embodiment will now be described.

The operation in the third embodiment is equal to those in the first and second embodiments in many aspects. Further, the operation in the third embodiment is different from those in the first and second embodiments in a method of changing the allowable range.

Figure 19:
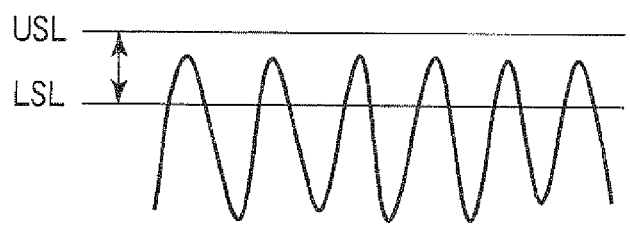
FIG. 19 is a view showing a setting example of an allowable range when a respiratory variation is small in a third embodiment.

In the third embodiment, the main controller 10g changes a width of the allowable range in accordance with a magnitude of an obtained index. Specifically, as shown in FIGS. 19 and 20, a width of the allowable range when a respiratory variation is large is reduced to be smaller than that of the allowable range when the respiratory variation is small.

According to this third embodiment, it is possible to prevent data collection in states having considerably different respiration levels from being carried out when the respiratory variation is increased.

This third embodiment is useful when image quality is more important than examination efficiency.

(Fourth Embodiment)

According to a fourth embodiment, a main controller 10g has a plurality of functions mentioned below. It is to be noted that the plurality of functions can be realized by allowing a processor included in the main controller 10g to execute a program.

One of the functions is to control each relevant portion in such a manner that a monitoring NMR signal is acquired by a data collection unit 10b. One of the functions is to detect a respiration level of a subject 200 based on a monitoring NMR signal acquired by the data collection unit 10b. One of the functions is to control each relevant portion in such a manner that a reconstruction NMR signal is collected by the data collection unit 10b when the rate of change in the detected respiration level is less than or equal to a predetermined rate.

An operation of the MRI apparatus 100 according to the fourth embodiment will now be described.

In the fourth embodiment, the sequence depicted in FIG. 5 is applied like the first embodiment.

Furthermore, the main controller 10g executes processing shown in FIG. 21 every time an MPP is acquired.

At step Sb1, the main controller 10g measures a speed of the diaphragm. Specifically, a current respiration level is first detected based on the newly acquired MPP. Moreover, the main controller 10g measures a current speed of the diaphragm based on a state of a change of the respiration level detected here from a respiration level detected in the past. Specifically, when the continuously detected two respiration levels are represented as Li and Li+1 and an elapsed time until Li+1 is detected after these two respiration levels Li are detected is represented as $\Delta t$, a speed V of the diaphragm can be calculated based on the following expression:

$$V = (Li+1 - Li)/\Delta t$$

It is to be noted that, when the sequence depicted in FIG. 5 is adopted, $\Delta t$ corresponds to an interval of R–R in an electrocardiogram.

At step Sb2, the main controller 10g confirms whether the speed measured at step Sb1 is less than or equal to a specified speed. The specified speed is previously determined to be an arbitrary value sufficiently smaller than a maximum speed of the diaphragm.

When the speed of the diaphragm is less than or equal to the specified speed, the main controller 10g advances to step Sb3 from step Sb2. Further, at step Sb3, the main controller 10g controls each relevant portion in such a manner that the reconstruction NMR signal is collected by the data collection unit 10b.

However, when the speed of the diaphragm is not less than or equal to the specified speed, the main controller 10g terminates the processing in FIG. 21 without collecting the reconstruction NMR signal.

Thus, only when the current speed of the diaphragm obtained from the MPP is sufficiently small, data is collected during a subsequent data collection period. Here, the speed of the diaphragm is zero when the respiration level achieves a peak. Therefore, data collection is performed only when the respiration level is close to the peak. Such an operation is equivalent to a situation where a threshold SL is changed in accordance with a change in the respiration level and the data collection is performed only when the respiration level exceeds this threshold SL as shown in FIG. 22.

As explained above, according to the fourth embodiment, the imaging can be continued even though the respiration level changes.

(Fifth Embodiment)

According to a fifth embodiment, a main controller 10g has a plurality of functions mentioned below. It is to be noted that the plurality of functions can be realized by allowing a processor included in the main controller 10g to execute a program.

One of the functions is to control each relevant portion in such a manner that a monitoring NMR signal is acquired by a data collection unit 10b. One of the functions is to detect a respiration level of a subject 200 based on the monitoring NMR signal acquired by the data collection unit 10b. One of the functions is to control each relevant portion in such a manner that a reconstruction NMR signal is collected by the data collection unit 10b when the detected respiration level falls within an allowable range. One of the functions is to repeatedly detect the peak value of the detected respiration level in 1 cycle of a respiratory operation of the subject 200. One of the functions is to set the allowable range based on the average value of peak values detected during a first period (a later-described N2 heartbeat). One of the functions is to calculate the variation of peak values based on a plurality of peak values detected in each of a plurality of second periods (e.g., periods during which continuous 2 peak values are detected). One of the functions is to set a length of the first period in accordance with a frequency that the calculated variation exceeds a reference value during a third period (a later-described N3 heartbeat).

An operation of the MRI apparatus 100 according to a fifth embodiment will now be described.

In the fifth embodiment, the sequence depicted in FIG. 5 is applied to the imaging like the first embodiment, for example.

Figure 23:
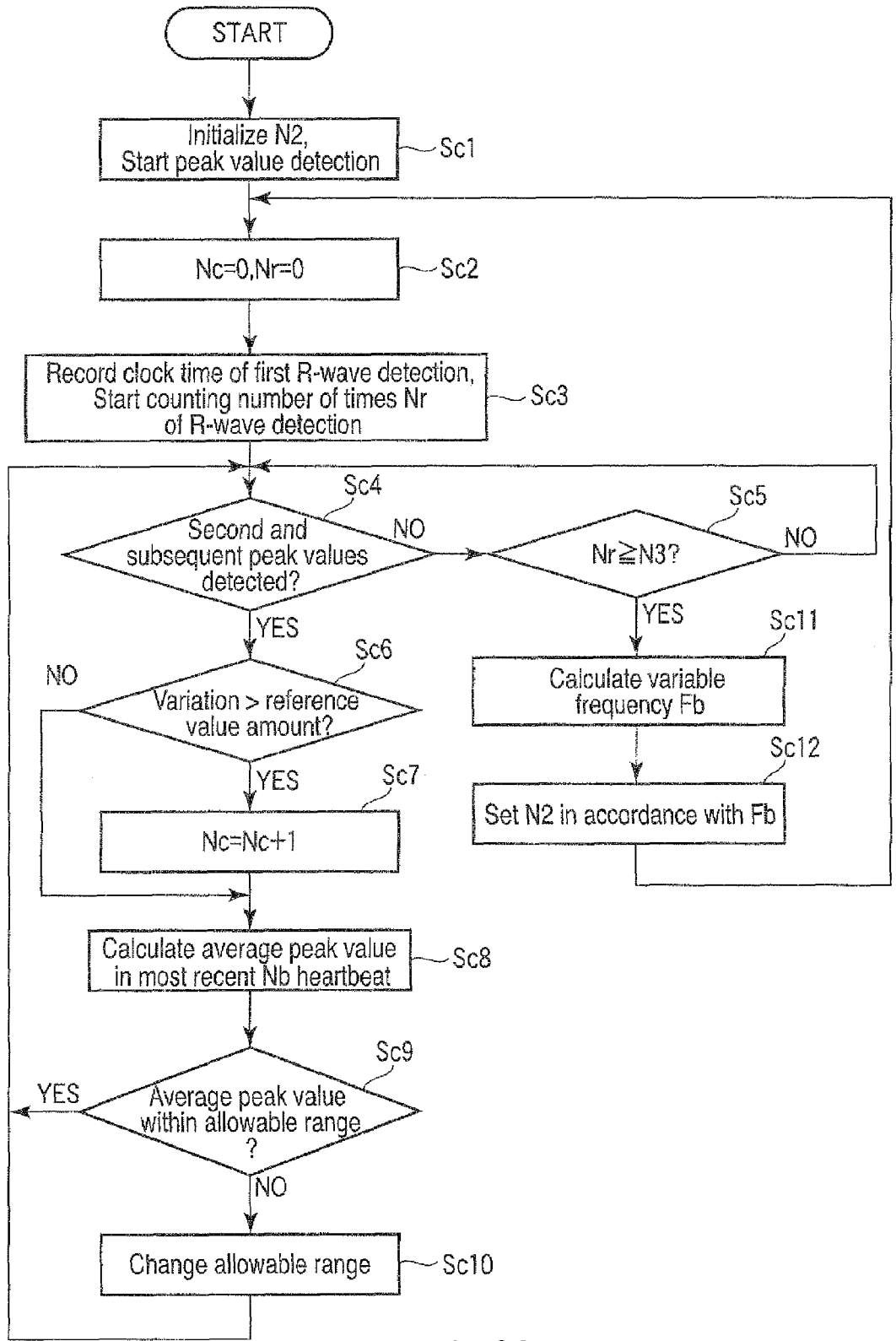
FIG. 23 is a view showing a processing procedure of the main controller depicted in FIG. 4 according to a fifth embodiment.

The main controller 10g executes such processing as depicted in FIG. 23 in parallel to execution of the imaging.

At step Sc1, the main controller 10g initializes a variable N2 to a preset initial value and starts the detection of the peak value. As the variable N2, three values, i.e., N2 fast, N2 middle, and N2 slow can be taken. However, a relationship N2 fast<N2 middle<N2 slow is achieved. In this case, any one of N2 fast, N2 middle, and N2 slow can be used as the initial value for the variable N2. Since processing for detecting the peak value is the same as that in the first embodiment, a description thereof will be omitted. It is to be noted that, when the number of points of respiration levels to which reference is made to detect peak values is represented as N1, the variable N2 is determined so that a relationship N1<N2 is constantly achieved.

Further, the main controller 10g executes the following processing in parallel to detection of the peak value.

At step Sc2, the main controller 10g clears both a variable Nc and a variable Nr to zero.

At step Sc3, the main controller 10g records a first clock time an R-wave detection signal is input after shifting to this step Sc3 in a memory 10d or an internal memory, and starts counting the number of times of detecting R-wave. The counting the number of times of detecting the R-wave is processing of counting up the variable Nr every time a subsequent R-wave detection signal is input. This processing is executed in parallel to the above-described peak value detection processing and processing explained below.

At step Sc4 and step Sc5, the main controller 10g detects a second or subsequent peak value after starting the peak value detection at step Sc1, or waits until the variable Nr becomes a preset value N3 or a higher value.

When the second or subsequent peak value is detected, the main controller 10g advances to step Sc6 from step Sc4. Further, at step Sc6, the main controller 10g confirms whether the variation of peak values obtained as the difference between a newly detected peak value and a previously detected peak value is higher than a preset reference amount.

Figure 24:
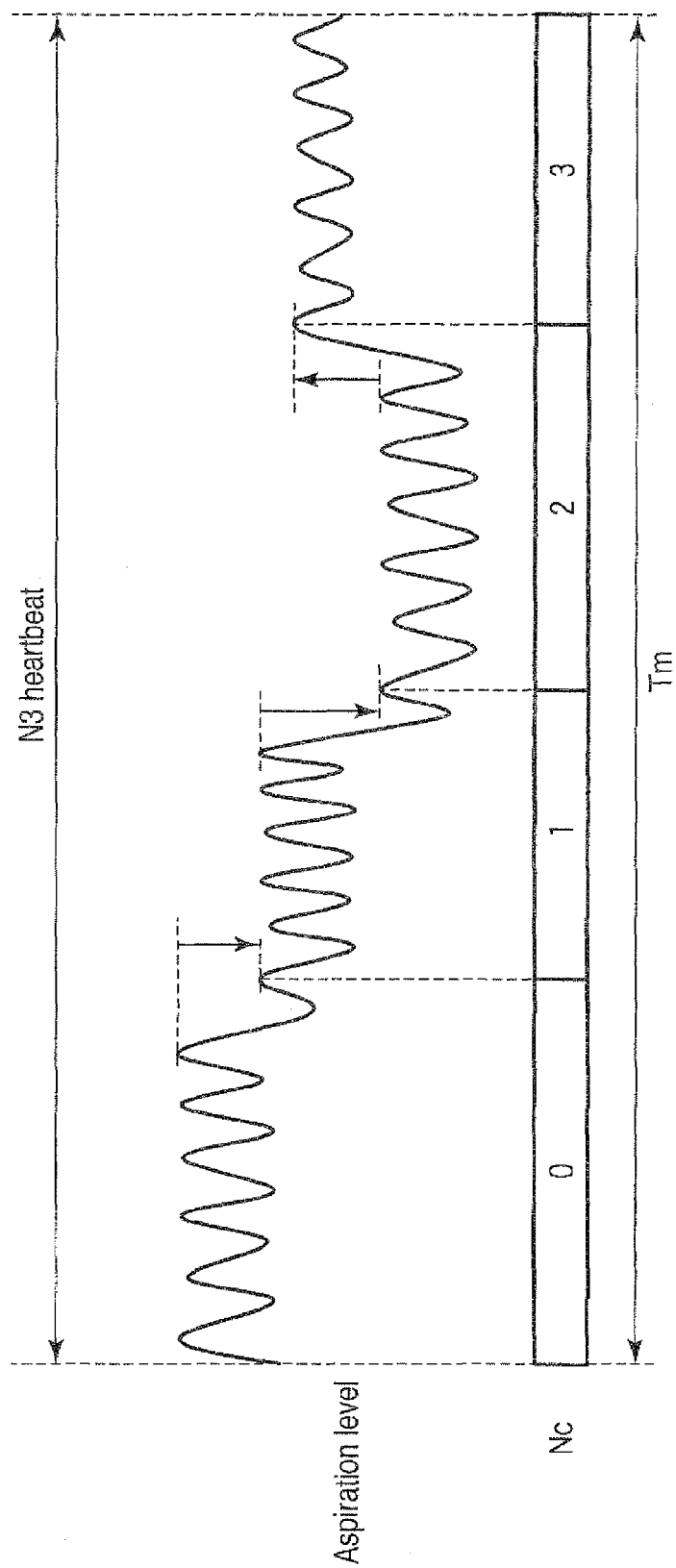
FIG. 24 is a view showing an example of a change in variable Nc.

When the variation is higher than the reference amount, the main controller 10g advances to step Sc7 from step Sc6. Moreover, at step Sc7 the main controller 10g increments the variable Nc by 1. Thereafter, the main controller 10g advances to step Sc8 from step Sc7. It is to be noted that, when the variation is less than the reference amount, the main controller 10g skips step Sc7 and directly advances to step Sc8 from step Sc6. Thus, as shown in FIG. 24, the variable Nc becomes a count value of the number of times that a considerable peak value fluctuation that the difference between two continuously detected peak values exceeds a reference value, i.e., a respiratory variation occurs.

At step Sc8, the main controller 10g calculates the average value of peak values detected during the most recent N2 heartbeat (which will be referred to as the average peak value hereinafter).

At step Sc9, the main controller 10g confirms whether the average peak value fails within an allowable range.

When the average peak value is out of the allowable range, the main controller 10g proceeds to step Sc10 from step Sc9. At step Sc10, the main controller 10g changes the allowable range based on the average peak value. The allowable range changed at this moment may be determined like the first embodiment, for example. Additionally, the main controller 10g returns to a standby state at step Sc4 and step Sc5.

It is to be noted that, when the average peak value falls within the allowable range, the main controller 10g returns to the standby state at step Sc4 and step Sc5 without executing the processing at step Sc10. Therefore, in this case, the allowable range is not changed.

Meanwhile, when the variable Nr becomes the value N3 or a higher value, the main controller 10g proceeds to step Sc11 from step Sc5. Further, at step Sc11, the main controller 10g calculates a variable frequency Fb based on the following expression:

$$Fb = Nc/(Tend - Tstart)$$

It is to be noted that Tend is a clock time that R-wave detection which serves as a trigger for counting up Nr to N3 is performed and Tstart is a clock time recorded at step Sc3. That is, the variable frequency Fb is calculated as a percentage of occurrences of a fluctuation in peak value where variation exceeds a reference amount during a period required for detecting the R-wave N3 times.

At step Sc12, the main controller 10g sets the variable N2 in accordance with the variable frequency Sb calculated as described above. Although a relationship between the variable frequency Fb and the variable N2 may be arbitrarily determined as, e.g., a value set by a designer of the MRI apparatus 100, a value set by an installation operator or a maintenance operator, or a value set by a user, is basically set in such a manner that the variable N2 is reduced as the variable frequency Fb is decreased. For example, 2 thresholds TH1 and TH2 having a relationship TH1>TH2 are determined in advance, N2 is determined as N2 fast if Fb>TH1, N2 is determined as N2 middle if TH1≥Fb>TH2, and N2 is determined as N2 slow if FB≤TH2. It is to be noted that, to obtain sufficient control characteristics, setting each of the values N2 fast, N2 middle and N2 slow to satisfy a relationship Fc=1/(THi×RR)>Fb based on the relationship of the thresholds TH1 and TH2 is desirable. However, i is 1 or 2, and RR is an R-wave detection interval. It is to be noted that, when the variable frequency Fb of the respiration level is low, high Fe may be maintained for the control system but, on the other hand, no fluctuation in threshold is ideal for movement correction. Therefore, when values sufficient for response characteristics Fe of the control system are maintained and a frequency of changing the allowable range is maintained at a minimum necessary level, assuring a more appropriate movement correction can be expected.

When setting the value N2 is finished in this manner, the main controller 10g returns to step Sc2 and repeats subsequent processing like the foregoing embodiment. As a result, the value N2 is set in accordance with a frequency of respiratory variations in each of periods which is required for detecting the R-wave for N3 times alone. Further, at step Sc8, the main controller 10g applies the most recent set value N2. As a result, the number of points of peak values to which reference is made to calculate the average peak value is changed in accordance with the frequency of respiratory variations.

As explained above, according to the fifth embodiment, the allowable range is frequently changed based on the average peak value calculated during a shorter period as the frequency of respiratory variations is high. Therefore, the allowable range is changed to follow the respiratory variations even though the frequency of respiratory variations is high, and the allowable range can be maintained as an appropriate range. On the other hand, when respiration is stable, the allowable range can be maintained at a required minimum allowable range change frequency rather than unnecessarily changing the allowable range, thereby enabling assuring an optimum movement correction accuracy.

(Sixth Embodiment)

According to a sixth embodiment, a main controller $10g$ has a plurality of functions mentioned below. It is to be noted that the plurality of functions can be realized by allowing a processor included in the main controller $10g$ to execute a program.

One of the functions is to control each relevant portion in such a manner that an NMR signal that is used for detecting a respiration level of a subject 200 (which will be referred to as a monitoring NMR signal hereinafter) is acquired by a data collection unit $10b$. One of the functions is to detect a respiration level of the subject 200 based on the monitoring NMR signal acquired by the data collection unit $10b$. One of the functions is to control each relevant portion in such a manner that an NMR signal that is used for reconfiguring an image (which will be referred to as a reconstruction NMR signal hereinafter) is collected by the data collection unit $10b$ when the detected respiration level falls within an allowable range. One of the functions is to repeatedly detect peak values of the detected respiration levels in 1 cycle of a respiratory motion of the subject 200. One of the functions is to set a trackable range based on the respiration level detected at the start of collecting the reconstruction NMR signal or at earlier timings. One of the functions is to set the allowable range within the trackable range based on the average value of peak values during a period wherein a plurality of respiration levels are detected.

An operation of the MRI apparatus 100 according to the sixth embodiment will now be described hereinafter.

In the sixth embodiment, prescan is carried out to initialize an allowable range. This prescan is performed to collect the monitoring NMR signal prior to starting main scan for collection of the reconstruction NMR signal. In regard to this prescan, the sequence depicted in FIG. 5 can be applied as it is or with data collection being omitted. It is to be noted that a period during which this prescan is carried out may be arbitrary as long as it is a period during which respiration levels at a sufficient number of points required for detecting the average peak value can be detected. As this prescan, prescan which has been already carried out in an existing MRI apparatus for another purpose may be used.

Figure 25:
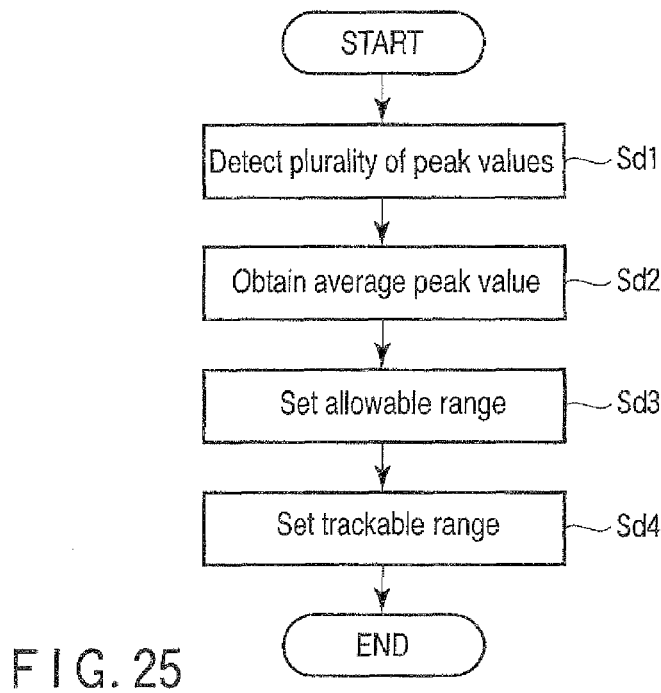
FIG. 25 is a view showing a processing procedure in a state where prescan of the main controller depicted in FIG. 4 is executed in a sixth embodiment.

The main controller $10g$ executes processing shown in FIG. 25 in a state where this prescan is effected.

At step Sd1, the main controller $10g$ detects a plurality of peak values from the respiration levels detected during the prescan. A technique for detecting the peak values may be the same as that in the first embodiment.

Moreover, when the prescan is terminated, the main controller $10g$ advances to step Sd2 from step Sd1. Additionally, at step Sd2, the main controller $10g$ obtains the average peak value of the plurality of peak values detected during the prescan period.

At step Sd3, the main controller $10g$ sets an allowable range based on the obtained average peak value. This setting of the allowable range can be performed based on a preset rule, and this rule may be arbitrary. For example, the allowable range having a fixed width can be determined with the average peak value being set as a central level. That is, the above-described processing can be applied in relation to the processing at step Sa4 in FIG. 6.

Figure 27:
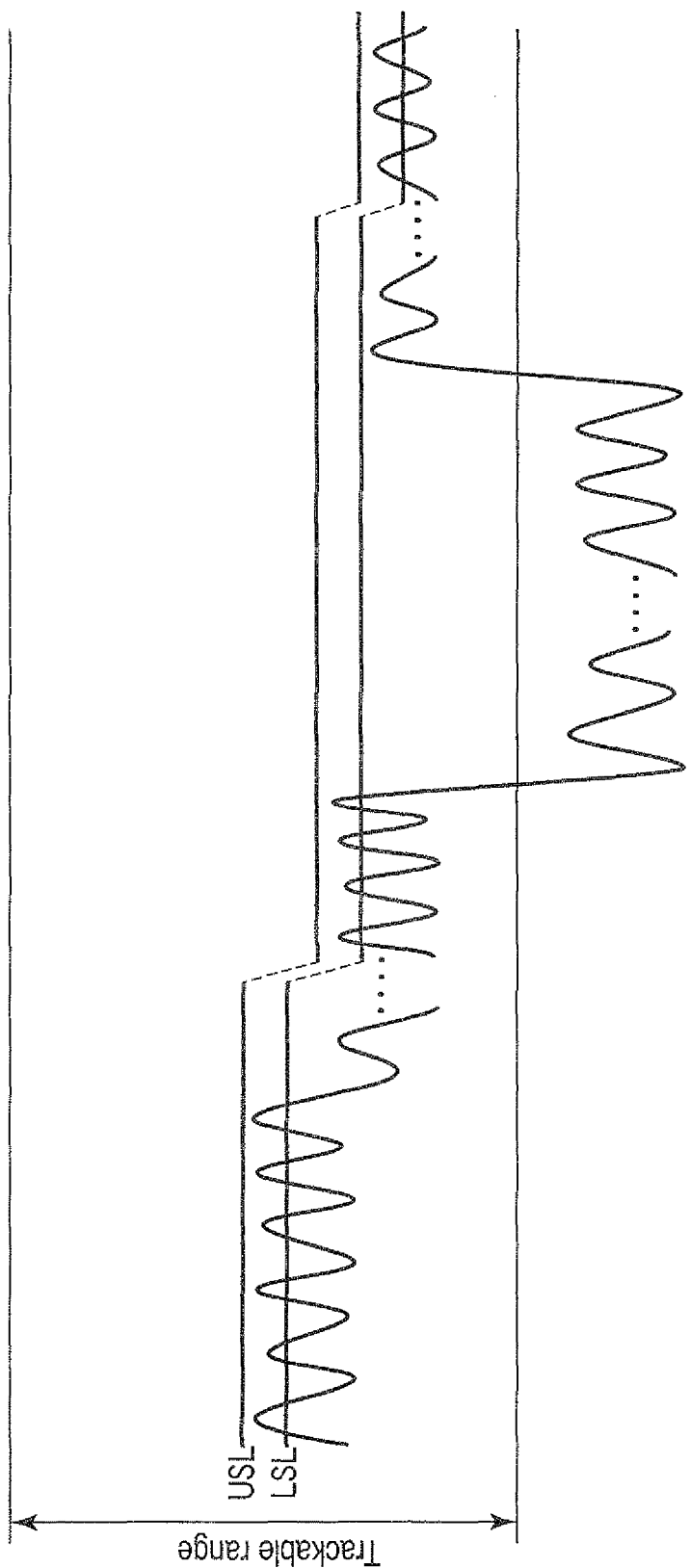
FIG. 27 is a view showing an example of a change in allowable range and a trackable range in the sixth embodiment.

At step Sd4, the main controller $10g$ sets a trackable range based on the allowable range set as explained above. This setting of the trackable range can be carried out based on a preset rule, and this rule may be arbitrary. For example, as shown in FIG. 27, the trackable range can be set as a range obtained by adding a margin having a fixed width each of upper and lower sides of the allowable range.

Meanwhile, when the prescan is terminated and the setting of the allowable range and the trackable range is completed, the main scan is started. The main scan is effected by WH-MBCA utilizing the RMC method, and the sequence depicted in FIG. 5 is applied, for example.

Figure 26:
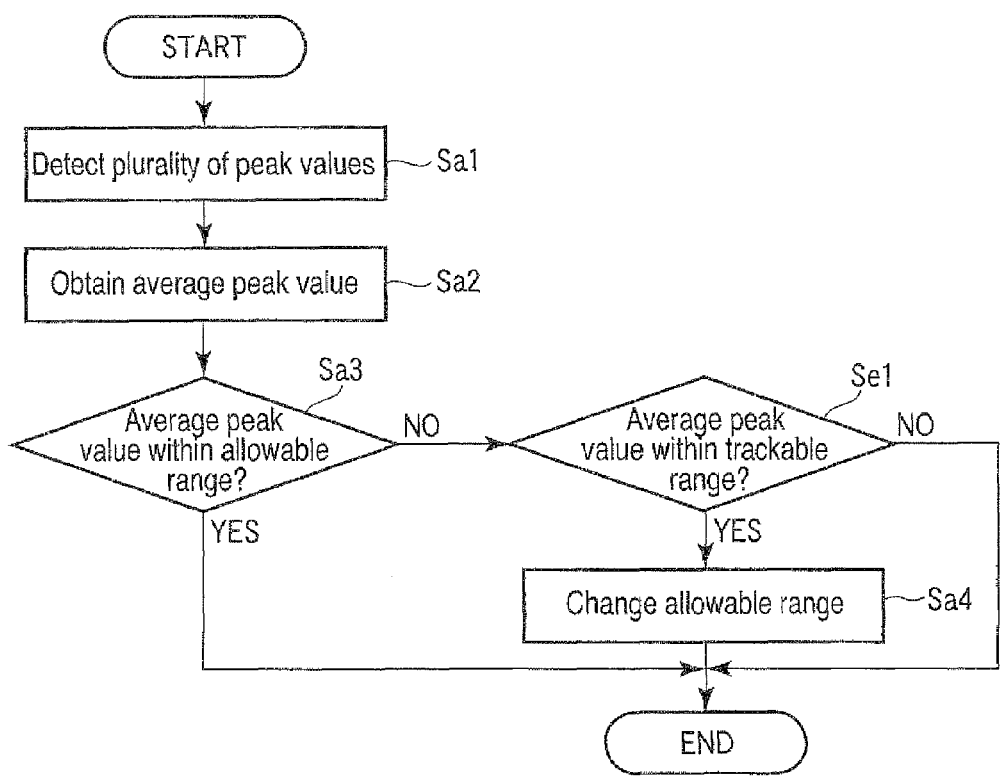
FIG. 26 is a view showing a processing procedure in a state where main scan of the main controller depicted in FIG. 4 is executed in the sixth embodiment.

Additionally, the main controller $10g$ executes such processing as shown in FIG. 26 at each predetermined timing in parallel to execution of the main scan. Although the timing for executing this processing may be arbitrary, executing the processing each time the new respiration level is detected or each time a fixed time elapses can be considered. It is to be noted that, in FIG. 26, like reference numerals denote steps equal to those shown in FIG. 6, thereby omitting a detailed description thereof.

The main controller $10g$ carries out step Sa1 to step Sa3 like the first embodiment. Further, when the average peak value is out of the allowable range, the main controller $10g$ advances to step Se1 from step Sa3.

At step Se1, the main controller $10g$ confirms whether the average peak value obtained at step Sa1 falls within the trackable range set at step Sd4 in FIG. 25.

When the average peak value falls within the trackable range, the main controller $10g$ proceeds to step Sa4 from step Se1 to change the allowable range like the first embodiment. However, when the average peak value is out of the trackable range, the main controller $10_g$ terminates the processing in FIG. 26 without executing step Se1 to step Sa4.

As explained above, in the sixth embodiment, the allowable range and the trackable range are set based on the respiration level immediately before starting the main scan, respectively. Furthermore, the allowable range is changed in accordance with the average peak value only when the average peak value falls within the trackable range, and the allowable range is not changed as shown in, e.g., FIG. 27 when the average peak value is out of the trackable range. Therefore, when a variation of the respiration level immediately before starting the main scan increases so that the average peak value deviates from the trackable range, the allowable range is not changed in accordance with such an average peak value. Therefore, a state wherein each peak value of the respiration level is out of the allowable range continues, and the NMR signal effective for image reconstruction is not collected. That is, since the shape of the heart may be different from the shape at the beginning of the main scan in the state wherein the respiration level greatly fluctuates, the NMR signal collected in such a state is not used for image reconstruction, thereby assuring excellent image quality.

This embodiment can be modified in many ways as follows.

The respiration level may be detected by a different unit. For example, a respiratory synchronization sensor or an expiratory meter can be used. However, the respiratory synchronization sensor is disposed to an abdominal region of the subject 200 and detects respiration level based on physical movement of the abdominal region.

At step Sa3 in the first embodiment, a range different from the allowable range may be determined, and whether the average peak value falls within this range may be confirmed.

Step Sa3 in the first embodiment may be omitted. That is, the allowable range may be again set based on a newly obtained average peak value no matter what the average peak value is.

In the first to sixth embodiments, the display system 12 may display an image that enables the subject 200 to recognize how the allowable change has been changed. When this configuration is adopted, the subject 200 can adjust his/her respiration in such a manner that the peak of the respiration level is adapted to the changed allowable range. It is to be noted that, when such display is not performed, the image transmission system 11 and the display system 12 do not have to be provided.

The second or third embodiment can be combined with the first embodiment to be carried out.

When the second and the third embodiments are selectively carried out in accordance with a desire of a user, an operation where examination efficiency is important and an operation where image quality is important can be separately used depending on the user's needs, which is convenient.

In the fifth embodiment, a reference number of points for N2 previously determined by an operator may be selected in accordance with a respiratory variation state of the subject 200 rather than completely automatically selecting the value N2. As a result, the respiration level can be excellently followed even though a frequency of respiration level variations of the subject 200 changes. Further, the required minimum allowable range change frequency can be maintained rather than unnecessarily changing the allowable range, thereby assuring an optimum movement correction accuracy.

In the fifth embodiment, the number of values which can be set as the value N2 may be 2 or may be not smaller than 4. Alternatively, the value N2 may be set as a continuous function of the variable frequency Fb. Specifically, for example, $Fc=1/(N2 \times RR) > Fb$ is set with respect to a change in frequency as a control target in such a manner that f characteristics are provided as a sufficient control system.

In the sixth embodiment, the trackable range may be set in accordance with a specification of a user. Alternatively, the main controller 10g may automatically set the trackable range based on the allowable range set in accordance with a specification of the user.

In the fifth and sixth embodiments, a period during which two peak values are detected is determined as the second period. Further, a variation is calculated as the difference between the two peak values detected during this period. However, the second period and the variation calculating method can be appropriately changed. For example, the second period may be determined as a period during which three or more peak values are detected, and a variation may be calculated as the difference between a minimum value and a maximum value of the three or more peak values detected during this period. Alternatively, the second period may be determined as a period during which two average peak values are detected, and a variation may be calculated as the difference between the two average peak values detected during this period.

Moreover, although the second period may be set to partially overlap a different second period in terms of time like the fifth and, sixth embodiments, it may be set in such a manner that it does not overlap the different second period in terms of time. For example, in the fifth and the sixth embodiments, a period during which an nth peak value and an n+1th peak value are detected and a period during which the n+1th peak value and an n+2th peak value are detected are the second periods, and these second periods partially overlap each other in terms of time. However, for example, assuming that the period during which the nth peak value and the n+1th peak value are detected is the preceding second period, the following second period may be determined as a period during which the n+2th peak value and an n+3th peak value are detected, and these second periods may be prevented from overlapping each other in terms of time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
    an MRI gantry and associated control circuits including at least one computer configured to collect magnetic resonance signals from a subject by applying a uniform static magnetic field, radio-frequency magnetic fields, and gradient magnetic fields to the subject in accordance with a predetermined pulse sequence;
    said control circuits including at least one computer configured to reconstruct an image concerning the subject based on the collected magnetic resonance signals;
    said control circuits being configured to detect a respiration level of the subject;
    said control circuits also being configured to control image reconstruction based on the collected magnetic resonance signals when a peak of the detected respiration level falls within an allowable range; and
    wherein said control circuits are configured to change the allowable range during an MRI scan which collects MRI signals from the subject in response to a change in a plurality of peak values of detected respiration levels.

2. The magnetic resonance imaging apparatus according to claim 1, wherein the control circuits are configured to shift a central level of the allowable range.

3. The magnetic resonance imaging apparatus according to claim 1, wherein the control circuits are configured to change a width of the allowable range.

4. The magnetic resonance imaging apparatus according to claim 1, wherein the control circuits are configured to change the allowable range based on a change in respiration peak level of the subject obtained from the detected respiration level.

5. The magnetic resonance imaging apparatus according to claim 1, wherein the respiration level is repeatedly detected, and
    the allowable range is changed based on an average value of peak values of the respiration level based on N, where N is an integer greater than or equal to 2, detected respiration levels.

6. The magnetic resonance imaging apparatus according to claim 5, wherein said control circuits are further configured:
    to obtain an index value for a fluctuation in respiratory status of the subject; and
    to change the value N based on the obtained index value.

7. The magnetic resonance imaging apparatus according to claim 6, wherein the index value is one of: (a) a variance of the respiration levels detected during a predetermined period, (b) an average value or a difference value of a variance of the respiration levels in predetermined two periods, and (c) the number of peak levels included in the respiration levels detected in a unit time.

8. The magnetic resonance imaging apparatus according to claim 1, wherein the image is reconstructed based on the collected magnetic resonance signals when a peak of the detected respiration level falls within the allowable range during a period that the subject holds his/her breath.

9. The magnetic resonance imaging apparatus according to claim 1, wherein the image is reconstructed based on the collected magnetic resonance signals when a peak of the detected respiration level falls within the allowable range irrespective of a period that the subject holds his/her breath or a period that subject naturally breathes.

10. A magnetic resonance imaging apparatus comprising:
an MRI gantry and associated control circuits including at least one computer configured to collect magnetic resonance signals from a subject by applying a uniform static magnetic field, radio-frequency magnetic fields, and gradient magnetic fields to the subject in accordance with a predetermined pulse sequence;
said control circuits including at least one computer configured to reconstruct an image concerning the subject based on the collected magnetic resonance signals;
said control circuits being configured to detect a respiration level of the subject; and
said control circuits also being configured to control collection and reconstruction of the magnetic resonance signals during an MRI scan which collects MRI signals from the subject when the rate of change of the detected respiration level is less than or equal to a predetermined rate, and to reconstruct the image in response to the thus collected magnetic resonance signals.

11. A magnetic resonance imaging apparatus comprising:
an MRI gantry and associated control circuits including at least one computer configured to collect magnetic resonance signals from a subject by applying a uniform static magnetic field, radio-frequency magnetic fields, and gradient magnetic fields to the subject in accordance with a predetermined pulse sequence;
said control circuits including at least one computer configured to reconstruct an image concerning the subject based on the collected magnetic resonance signals;
said control circuits being configured to repeatedly detect a respiration level of the subject;
said control circuits being configured to control the image reconstruction in response to the collected magnetic resonance signals when a peak of the detected respiration level falls within an allowable range;
said control circuits being configured to repeatedly detect peak values of the detected respiration level in one cycle of a respiratory motion of the subject;
said control circuits being configured to set the allowable range based on an average value of the peak values during a first period that the plurality of respiration levels are detected; and
said control circuits being configured to control the allowable range setting frequency during an MRI scan which collects MRI signals from the subject in accordance with a frequency of the respiratory motion of the subject and to set the allowable range at the setting frequency.

12. The magnetic resonance imaging apparatus according to claim 11, wherein the control circuits are further configured to:

calculate a variation of a plurality of peak values based on the plurality of detected peak values during each of a plurality of second periods which are set to cause the plurality of detected peak values and these second periods to be shifted from each other in terms of time; and
set a length of the first period in accordance with a frequency that the calculated variation exceeds a reference value during a third period longer than the second period.

13. The magnetic resonance imaging apparatus according to claim 11, wherein a central level of the allowable range is shifted.

14. The magnetic resonance imaging apparatus according to claim 11, wherein a width of the allowable range is changed.

15. The magnetic resonance imaging apparatus according to claim 11, wherein a period during which two peak values are detected is determined as the second period, and the variation as a difference between the two peak values is calculated.

16. The magnetic resonance imaging apparatus according to claim 11, wherein said control circuits are configured:
to accept input of a detection signal output every predetermined time phase by an electrocardiographic monitor which detects the predetermined time phase of a heartbeat concerning the subject,
to detect the respiration level in synchronization with the input detection signal, and
to determine a period during which a predetermined number of respiration levels are detected as the third period,
to measure a length of the third period based on intervals at which the detection signal is input during the third period, and
to calculate the frequency as a ratio of the length and a number of times that the calculated variation exceeds the reference value during the third period.

17. A magnetic resonance imaging apparatus, comprising:
an MRI gantry and associated control circuits including at least one computer configured to collect magnetic resonance signals from a subject by applying a uniform static magnetic field, radio-frequency magnetic fields, and gradient magnetic fields to the subject in accordance with a predetermined pulse sequence;
said control circuits including at least one computer configured to reconstruct an image concerning the subject based on the collected magnetic resonance signals;
said control circuits being configured to repeatedly detect a respiration level of the subject;
said control circuits being configured to image reconstruction based on the collected magnetic resonance signals when a peak of the detected respiration level falls within an allowable range;
said control circuits being configured to set a trackable range in response to the detected respiration level when or before starting collecting of the magnetic resonance signals which are used for image; and
said control circuits being configured to set the allowable range within the trackable range during an MRI scan which collects MRI signals from the subject based on an average value of the peak values during a period that the plurality of respiration levels are detected.

18. A magnetic resonance imaging method comprising:
collecting magnetic resonance signals from a subject by applying a uniform static magnetic field, radio-frequency magnetic fields, and gradient magnetic fields to the subject in accordance with a predetermined pulse sequence;

repeatedly detecting a respiration level of the subject during execution of said predetermined pulse sequence;
controlling image reconstruction based on magnetic resonance signals collected when a peak of the detected respiration level falls within an allowable range; and
changing the allowable range during an MRI scan which collects MRI signals from the subject in response to a change in a plurality of peak values of a plurality of detected respiration levels.

* * * * *